(12) United States Patent  
Dwivedi et al.

(10) Patent No.: US 9,249,134 B2  
(45) Date of Patent: Feb. 2, 2016

(54) PROCESS FOR PREPARATION OF AMORPHOUS FORM OF DASATINIB

(71) Applicant: CADILA HEALTHCARE LIMITED, Gujarat (IN)

(72) Inventors: Shriprakash Dhar Dwivedi, Gujarat (IN); Kumar Kamlesh Singh, Gujarat (IN); Nikhil Amar Singh, Gujarat (IN); Amol Kashinath Patil, Gujarat (IN)

(73) Assignee: Cadila Healthcare Limited, Gujarat (IN)

( * ) Notice: Subject to any disclaimer, the term of this patent is extended or adjusted under 35 U.S.C. 154(b) by 0 days.

(21) Appl. No.: 14/223,862

(22) Filed: Mar. 24, 2014

(65) Prior Publication Data

US 2014/0343073 A1 Nov. 20, 2014

(30) Foreign Application Priority Data

Mar. 26, 2013 (IN) .......................... 1126/MUM/2013  
Jul. 5, 2013 (IN) .......................... 2278/MUM/2013  
Aug. 23, 2013 (IN) .......................... 2759/MUM/2013

(51) Int. Cl.  
*C07D 417/14* (2006.01)  
*C07D 417/12* (2006.01)

(52) U.S. Cl.  
CPC ............ *C07D 417/12* (2013.01); *C07D 417/14* (2013.01)

(58) Field of Classification Search  
CPC ............................. C07D 417/14; A61K 31/427

USPC ...................................... 544/295; 514/252.19  
See application file for complete search history.

(56) References Cited

U.S. PATENT DOCUMENTS

2010/0256158 A1* 10/2010 Simo et al. ............... 514/252.19  
2010/0311751 A1* 12/2010 Schmitt et al. ............. 514/235.8  
2011/0306632 A1* 12/2011 Miller et al. .................. 514/293

* cited by examiner

*Primary Examiner* — Deepak Rao  
(74) *Attorney, Agent, or Firm* — William D. Hare; McNeely, Hare & War, LLP

(57) ABSTRACT

A stable amorphous form of dasatinib of Formula (I) wherein amorphous dasatinib after exposure to a relative humidity of 75% at 40 ° C. or 60% at 25 ° C. for a period of at least three months doesn't change to crystalline form and a process for the preparation of the amorphous form of dasatinib of Formula (I).

(I)

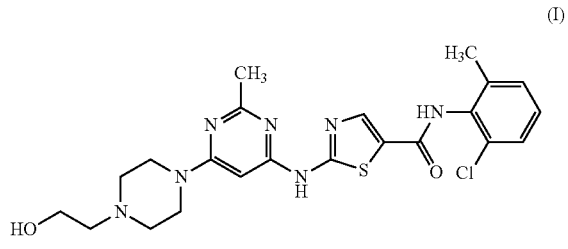

14 Claims, 12 Drawing Sheets

PROCESS FOR PREPARATION OF AMORPHOUS FORM OF DASATINIB

CROSS REFERENCE TO RELATED APPLICATIONS

Figure 1:
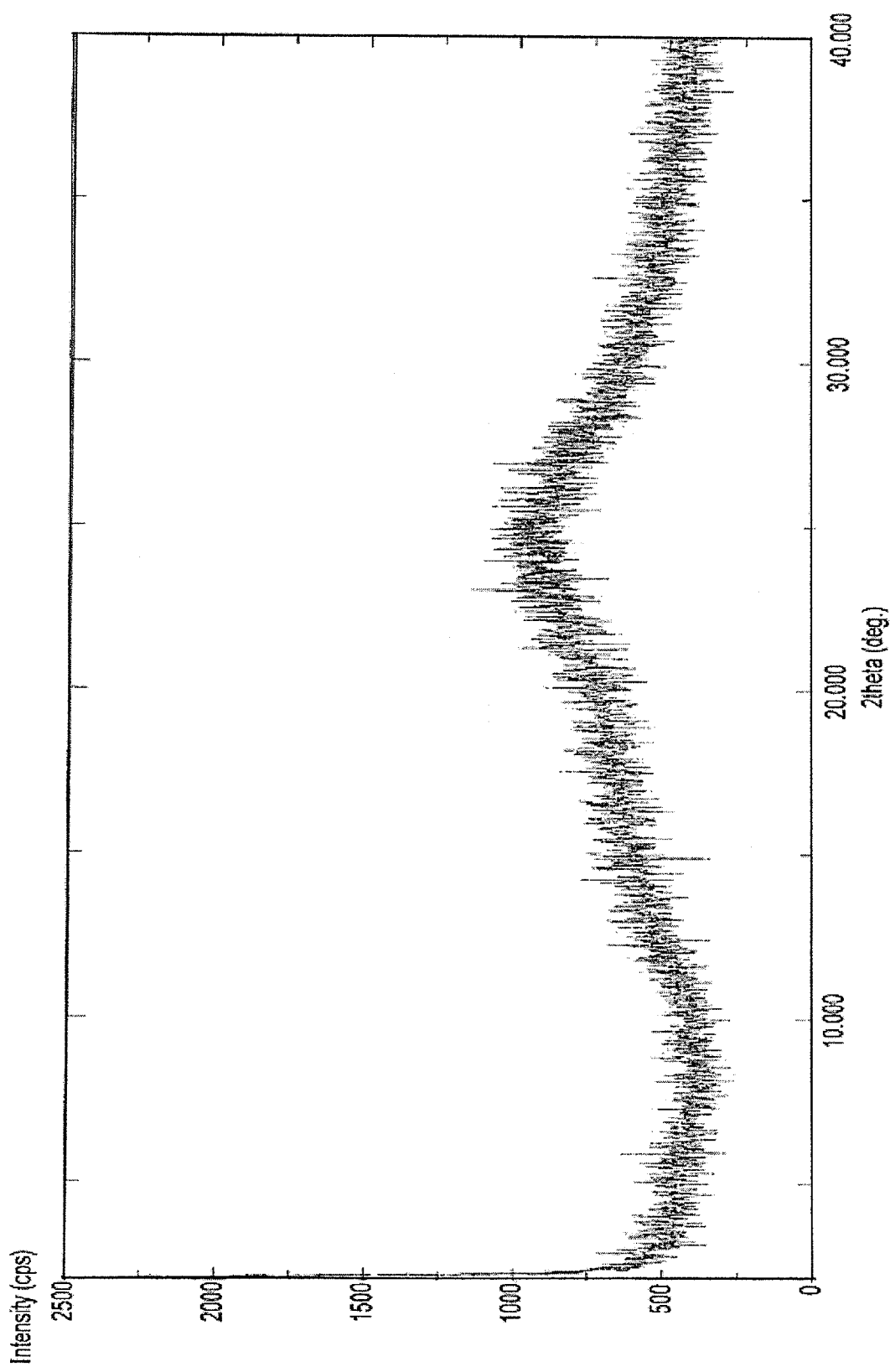

This application claims the priority to Indian Application No. 1126/MUM/2013, filed Mar. 26, 2013, Indian Application No. 2278/MUM/2013, filed Jul. 5, 2013, and Indian Application No. 2759/MUM/2013, filed Aug. 23, 2013, the entire contents of each which is hereby incorporated by reference.

FIELD OF THE INVENTION

The present invention relates to an improved process for the preparation of amorphous form of dasatinib of Formula (I). More particular the present invention relates to the pharmaceutical composition comprising a therapeutically effective amount of amorphous dasatinib together with one or more of pharmaceutically acceptable excipients used as protein tyrosine kinase-associated disorders.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Dasatinib is an oral protein tyrosine kinase inhibitor used to cure adult chronic myelogenous leukemia (CML), and acute lymphatic leukemia (ALL) with positive Philadelphia chromosome. It is available under the trade name of SPRYCEL® as kinase inhibitor indicated for the treatment of newly diagnosed adults with Philadelphia chromosome-positive (Ph+) chronic myeloid leukemia (CML) in chronic phase, adults with chronic, accelerated, or myeloid or lymphoid blast phase Ph+ CML with resistance or intolerance to prior therapy including imatinib and adults with Philadelphia chromosome-positive acute lymphoblastic leukemia (Ph+ All) with resistance or intolerance to prior therapy in the recommended dose of 20 mg, 50 mg, 70 mg, 80 mg, 100 mg and 140 mg tablets.

Dasatinib is chemically N-(2-chloro-6-methylphenyl)-2-[[6-[4-(2-hydroxyethyl)-1-piperazinyl]-2-methyl-4-pyrimidinyl]amino]-5-thiazolecarboxamide of Formula (I) and its monohydrate of Formula (IA) chemical structure is as below.

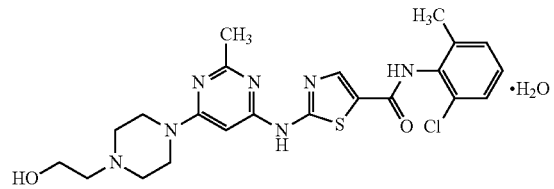

U.S. Pat. No. 6,596,746 B1 (the U.S. '746 Patent) discloses the process for the preparation of dasatinib (I) by reacting compound of Formula 3 with N-(2-hydroxyethyl)piperizine at 80° C. as shown in Scheme-1 as below.

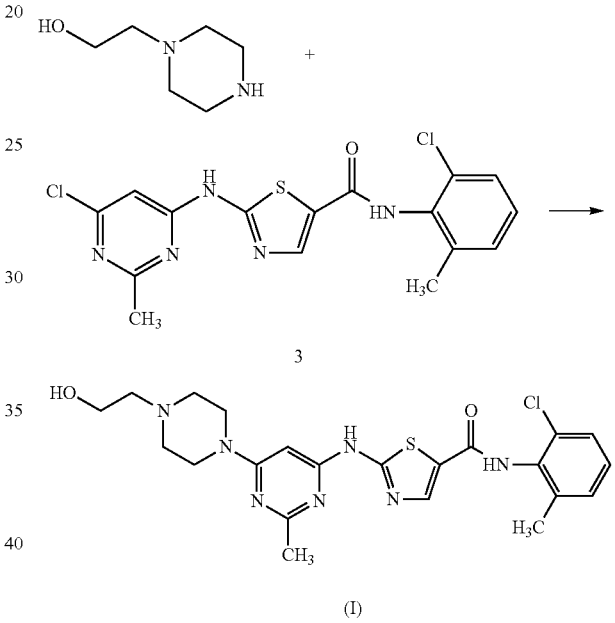

U.S. Pat. No. 7,491,725 B2 (the U.S. '725 B2 Patent) discloses dasatinib monohydrate and dasatinib butanol solvate and process for their preparation. Scheme-2 shows a general process for the preparation of Dasatinib as disclosed in the U.S. '725 B2. Intermediate 3 and N-(2-hydroxyethyl)piperazine are heated together in a solvent system comprising n-butanol as a solvent and diisopropyl-ethylamine (DIPEA) as a base. On cooling of the reaction mixture, Dasatinib precipitates out which is isolated by filtration.

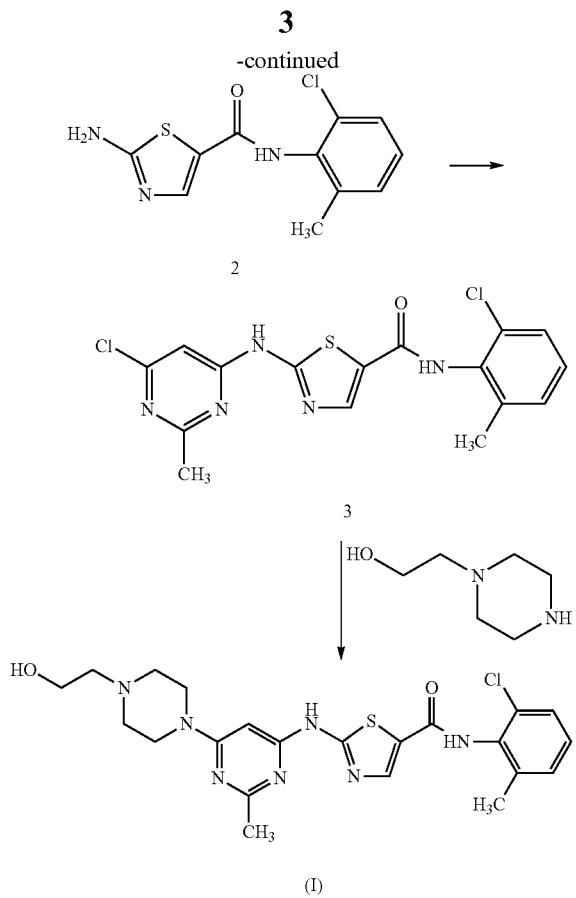

(I)

U.S. Pat. No. 8,242,270 B2 (the U.S. '270 Patent) discloses two ethanol solvates of dasatinib i.e. E2-1 and TIE2-1. The U.S. '270 patent also discloses two anhydrous forms of dasatinib i.e. N-6 and T1H1-7 and processes for their preparation.

U.S. Pat. No. 7,973,045 B2 (the U.S. '045 Patent) discloses various solvates and hydrates of dasatinib. In particular, the U.S. '045 patent discloses anhydrous Form-B, isopropanol solvate and acetone solvate for dasatinib.

The U.S. '045 patent also discloses the processes for the preparation of amorphous dasatinib. In particular, the example 26, 50, 56 and 60 discloses the process for the preparation of amorphous dasatinib. The example-26 discloses reacting compound 1, N-(2-hydroxyethyl)piperizine in presence of N-ethyldiisopropylamine in dimethylformamide at 90° C. The amorphous form was obtained by cooling the solution and dilution with water at 0° C. The example-26 when performed using the conditions provided therein resulted in amorphous dasatinib having residual DMF. The TGA of amorphous dasatinib discloses 48% loss of residual mass indicating higher residual solvents, which makes it unsuitable for pharmaceutical use.

The example 50, 56 and 60 discloses the processes for the preparation of amorphous dasatinib wherein dasatinib crystalline Form A21 was used as starting compound. Further, the solvents like 1,2-dichlorobenzene, benzyl alcohol and propyl glycol, respectively were used in examples 50, 56 and 60 wherein wet samples were analyzed for XRD to obtain amorphous form. However, the X-ray powder diffraction pattern as depicted in FIG. 35, FIG. 43 and FIG. 99 represented as amorphous dasatinib is a mixture of crystalline and amorphous form.

The example 50a further discloses that dasatinib amorphous obtained by example 50 (wet-cake) was dried in a bottle in a conventional oven overnight at 55° C. The obtained sample was analyzed by XRD and found to be Form BA, which is crystalline form. Therefore, the presence of residual solvents during drying will convert the amorphous form to crystalline form.

Therefore, the prior art process provides amorphous dasatinib containing higher amount of residual solvent which is not suitable for pharmaceutical developments. When the amorphous dasatinib having higher residual solvents is subjected to stability conditions, it is observed that it converts to crystalline form.

Therefore, the processes disclosed in the U.S. '045 patent may not be suitable for large scale preparation of amorphous dasatinib. The amorphous forms disclosed are not dry and may not be free from residual solvents. The samples were analyzed as wet-cake which is a mixture of crystalline and amorphous form.

U.S.PG-Pub. No. 2012/0309968 A1 discloses polymorph I of dasatinib monohydrate and polymorph II of dasatinib, their preparation methods and pharmaceutical compositions containing the same.

International (PCT) Publication WO 2013/065063 A1 discloses process for the preparation of anhydrous and monohydrate form of dasatinib which is incorporated herein as reference in its entirety.

Dasatinib is practically insoluble in water or organic solvents like methanol, ethanol, propanol, isopropanol, butanol and the like even in the condition of heating. Therefore, higher amount of solvents are required which is disadvantageous in industrial production. The method reported in the U.S. '725 B2 discloses use of ethanol and water mixture resulting in the formation of monohydrate.

The different physical properties exhibited by polymorphs affect important pharmaceutical parameters such as storage, stability, compressibility, density and dissolution rates (important in determining bioavailability). Stability differences may result from changes in chemical reactivity (e.g., differential hydrolysis or oxidation, such that a dosage form discolors more rapidly when comprised of one polymorph than when comprised of another polymorph), mechanical changes (e. g., tablets crumble on storage as a kinetically favored crystalline form converts to thermodynamically more stable crystalline form) or both (e. g., tablets of one polymorph are more susceptible to breakdown at high humidity). Solubility differences between polymorphs may, in extreme situations, result in transitions to crystalline forms that lack potency or are toxic. In addition, the physical properties of the crystalline form to that of an amorphous form may be important in pharmaceutical processing. For example, an amorphous form may provide better bioavailability than the crystalline form. Thus, a present amorphous form can provide a useful alternative for dasatinib monohydrate and may be useful for formulations which can have better stability, solubility, storage, compressibility etc important for formulation and product manufacturing and doesn't degrade to crystalline forms of dasatinib.

Therefore, it is desirable to have stable amorphous form of drugs with high purity to meet the needs of regulatory agencies and also highly reproducible processes for their preparation.

In view of the above, it is therefore, desirable to provide an efficient, more economical, less hazardous and eco-friendly process for the preparation of amorphous form of dasatinib. The amorphous form provided herein is at least stable under ordinary stability conditions with respect to purity, storage and is free flowing powder.

SUMMARY OF THE INVENTION

In one general aspect, there is provided an amorphous solid dispersion that includes dasatinib of Formula (I) and a polymer.

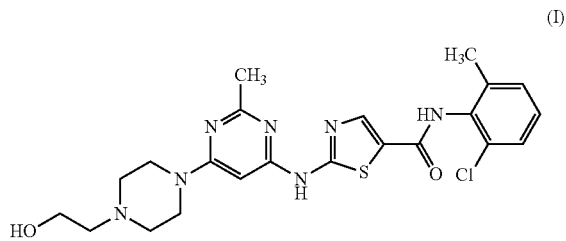 [SMILES: Cc1nc(Nc2ncc(C(=O)Nc3c(C)cccc3Cl)s2)cc(N2CCN(CCO)CC2)n1]

In another general aspect, there is provided an amorphous form of dasatinib of Formula (I) substantially free from residual solvents.

In another general aspect, there is provided a stable amorphous form of dasatinib of Formula (I) which is at least stable during storage and drying.

In another general aspect, there is provided a process for preparation of an amorphous form of dasatinib of Formula (I) by milling for sufficient time in absence of pharmaceutically acceptable carriers or polymers.

In another general aspect, there is provided a dispersion of an amorphous form of dasatinib of Formula (I) having at least one polymer, as well as methods for production of such dispersion from a solvent-based medium.

In another general aspect, there is provided a process for preparation of an amorphous form of dasatinib of Formula (I), which includes one or more of the following steps:
a) providing a solution of dasatinib composition in one or more of suitable solvent or mixture thereof; and
b) obtaining an amorphous form of dasatinib by removal of solvent.

In another general aspect, the stable amorphous dasatinib of Formula (I) is stored under nitrogen atmosphere and packed in a double polythene bag tied with a thread, keeping primary packing containing amorphous dasatinib inside a black color polyethylene bag containing oxygen busters and sealing it, placing above the double polyethylene bag inside a triple laminated bag optionally containing oxygen busters and sealing it, and placing the sealed triple laminated bag inside a closed high density polyethylene (HDPE) container and storing in controlled environment chamber at about 25° C. and/or 40° C.

In another general aspect, there is provided an amorphous dasatinib of Formula (I) having particle size distributions wherein the $10^{th}$ volume percentile particle size (D10) is less than about 50 µm, the 50th volume percentile particle size (D50) is less than about 200 µm, or the 90th volume percentile particle size (D90) is less than about 400 µm, or any combination thereof.

In another general aspect, there is provided an amorphous form of dasatinib of Formula (I) having an chiral purity of greater than about 95%, or greater than about 98%, or greater than about 99%, or greater than about 99.5%, or greater than about 99.8%, or greater than about 99.9%, as determined using high performance liquid chromatography (HPLC).

In another general aspect, there is provided a pharmaceutical composition comprising therapeutically effective amount of an amorphous form of dasatinib of Formula (I) together with one or more pharmaceutically acceptable carriers, excipients or diluents.

In another general aspect, there is provided a pharmaceutical composition comprising therapeutically effective amount of stable amorphous form of dasatinib of Formula (I) together with one or more pharmaceutically acceptable carriers, excipients or diluents.

In another general aspect, there is provided pharmaceutical composition comprising a stabilized composition of an amorphous form of dasatinib of Formula (I) together with one or more pharmaceutically acceptable carrier, optionally with one or more pharmaceutically acceptable excipients.

BRIEF DESCRIPTION OF THE ACCOMPANYING DRAWINGS

FIG. 1 discloses the x-ray diffractogram (XRD) of the amorphous form of dasatinib as per reference example-1

Figure 2:
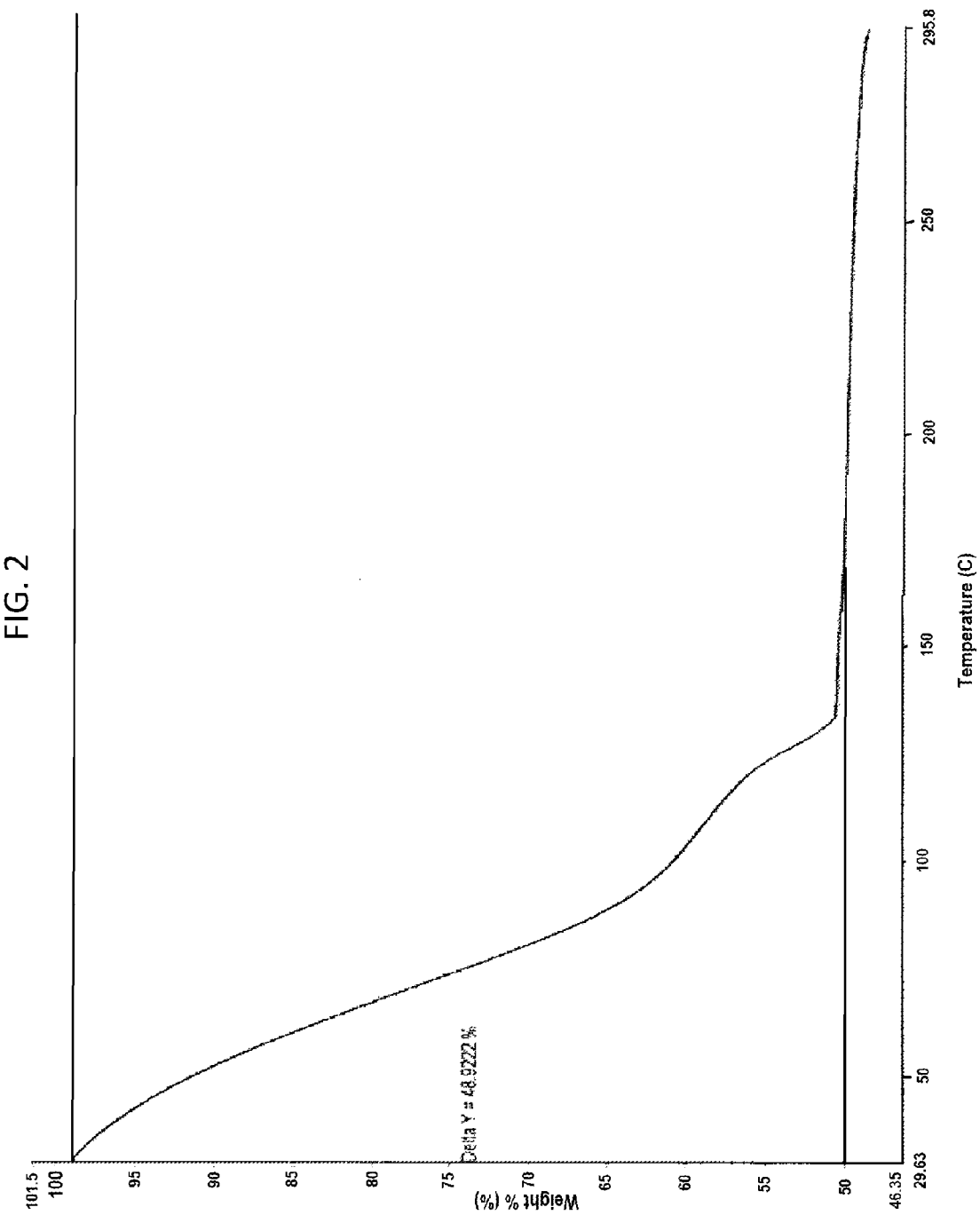

FIG. 2 discloses the thermogravimetric analysis (TGA) of the amorphous form of dasatinib as per reference example-1.

Figure 3:
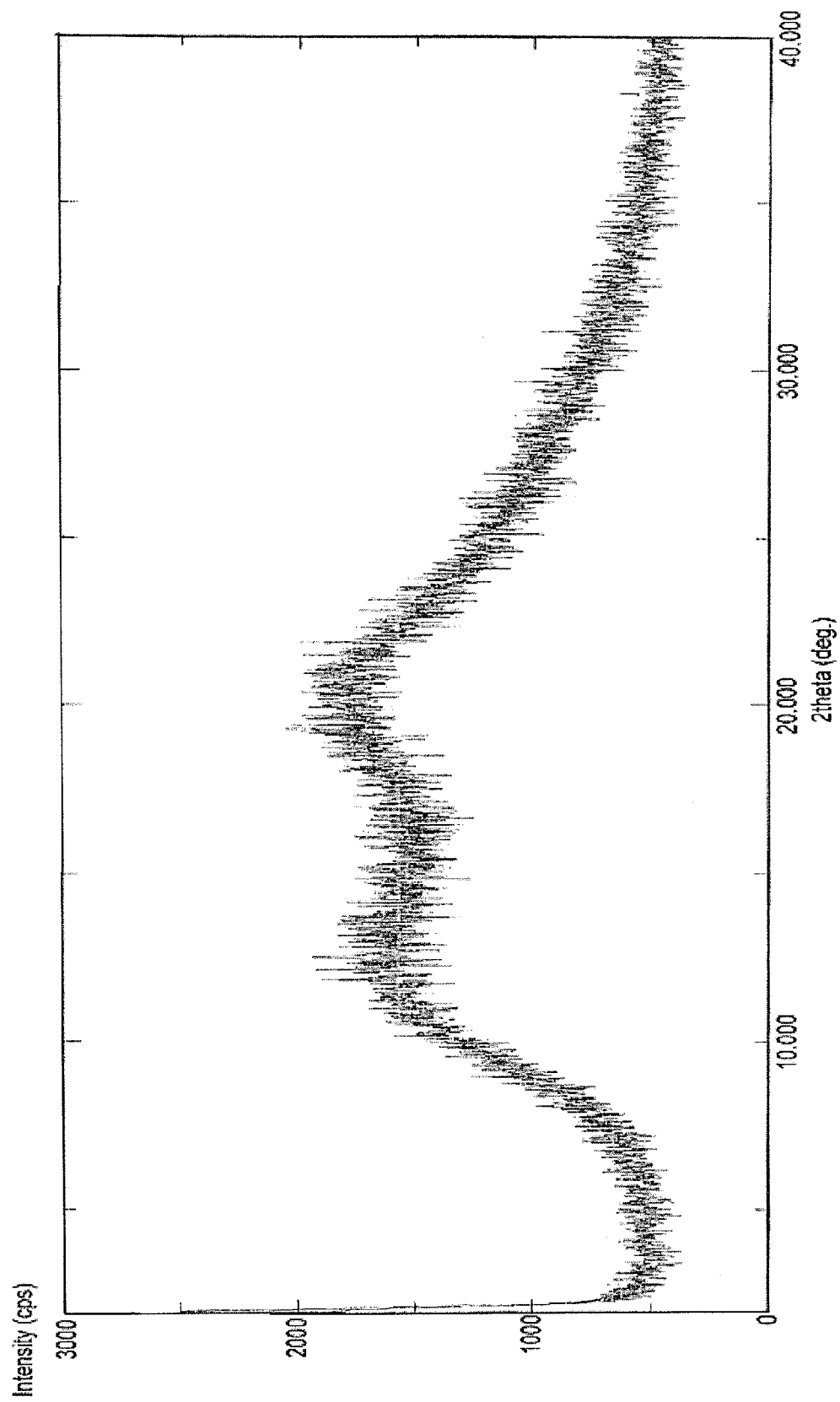

FIG. 3 discloses the x-ray diffractogram (XRD) of the amorphous form of dasatinib as per example-1.

Figure 4:
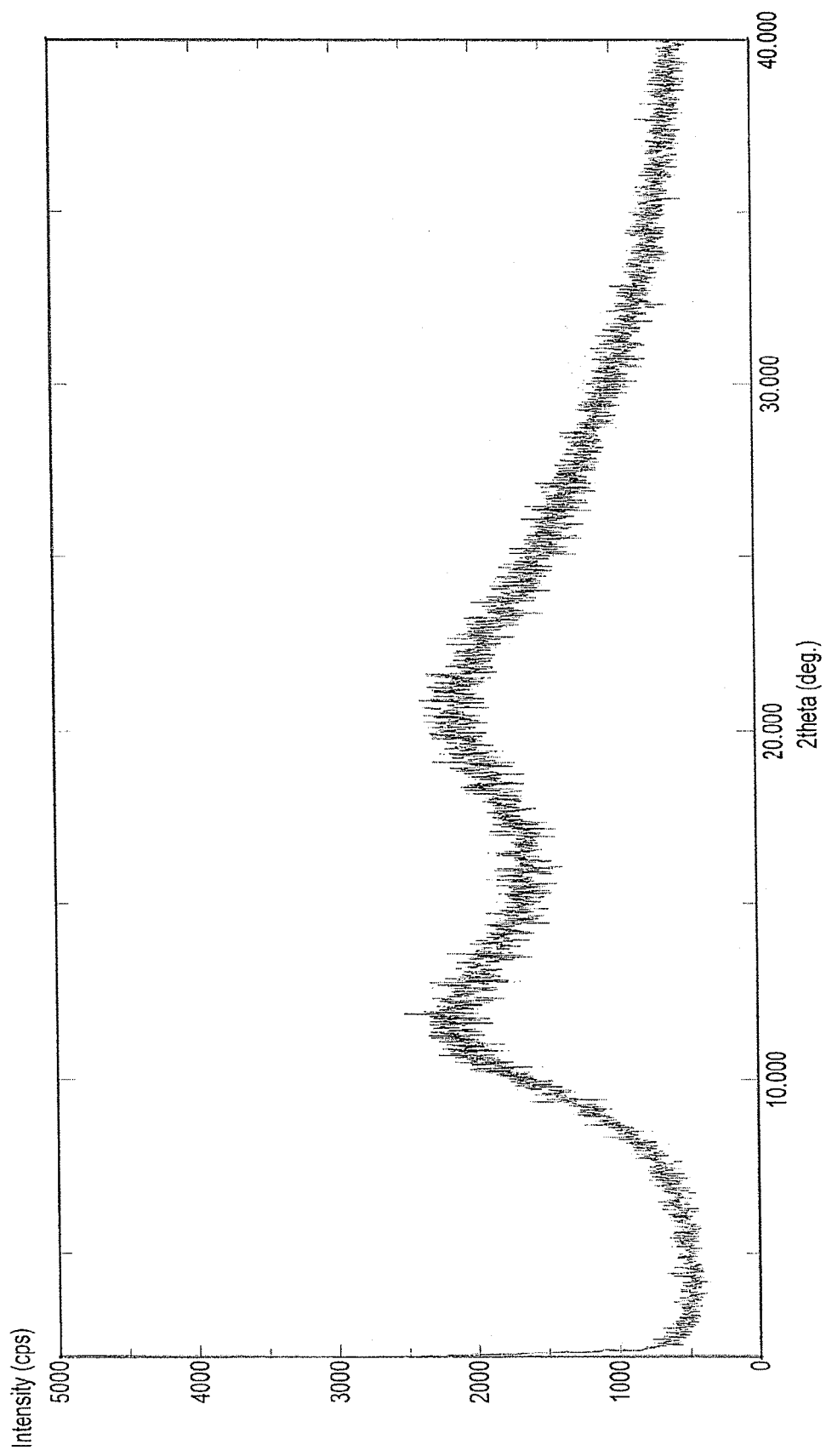

FIG. 4 discloses the x-ray diffractogram (XRD) of the amorphous form of dasatinib as per example-2.

Figure 5:
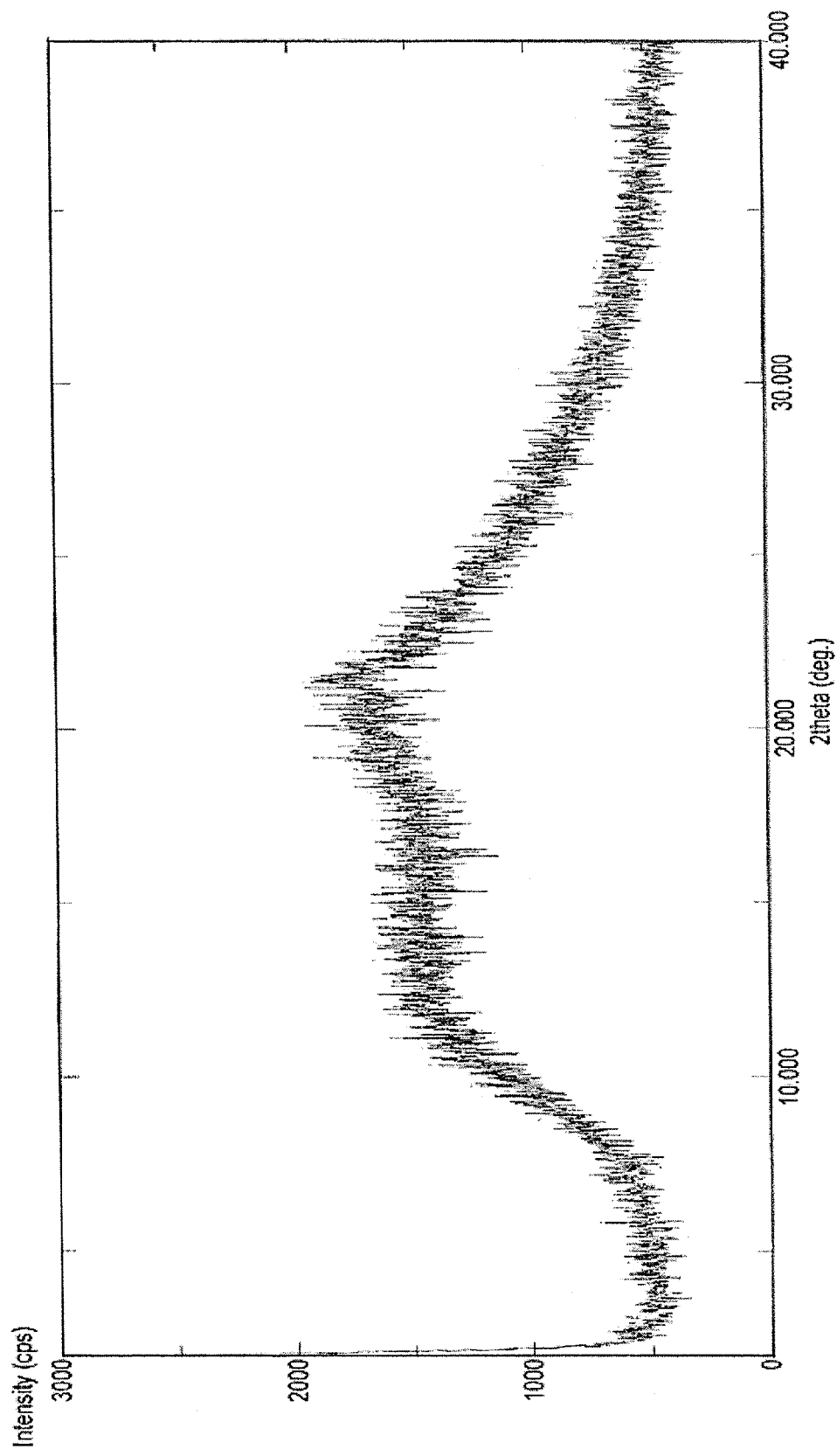

FIG. 5 discloses the x-ray diffractogram (XRD) of the amorphous form of dasatinib as per example-4.

Figure 6:
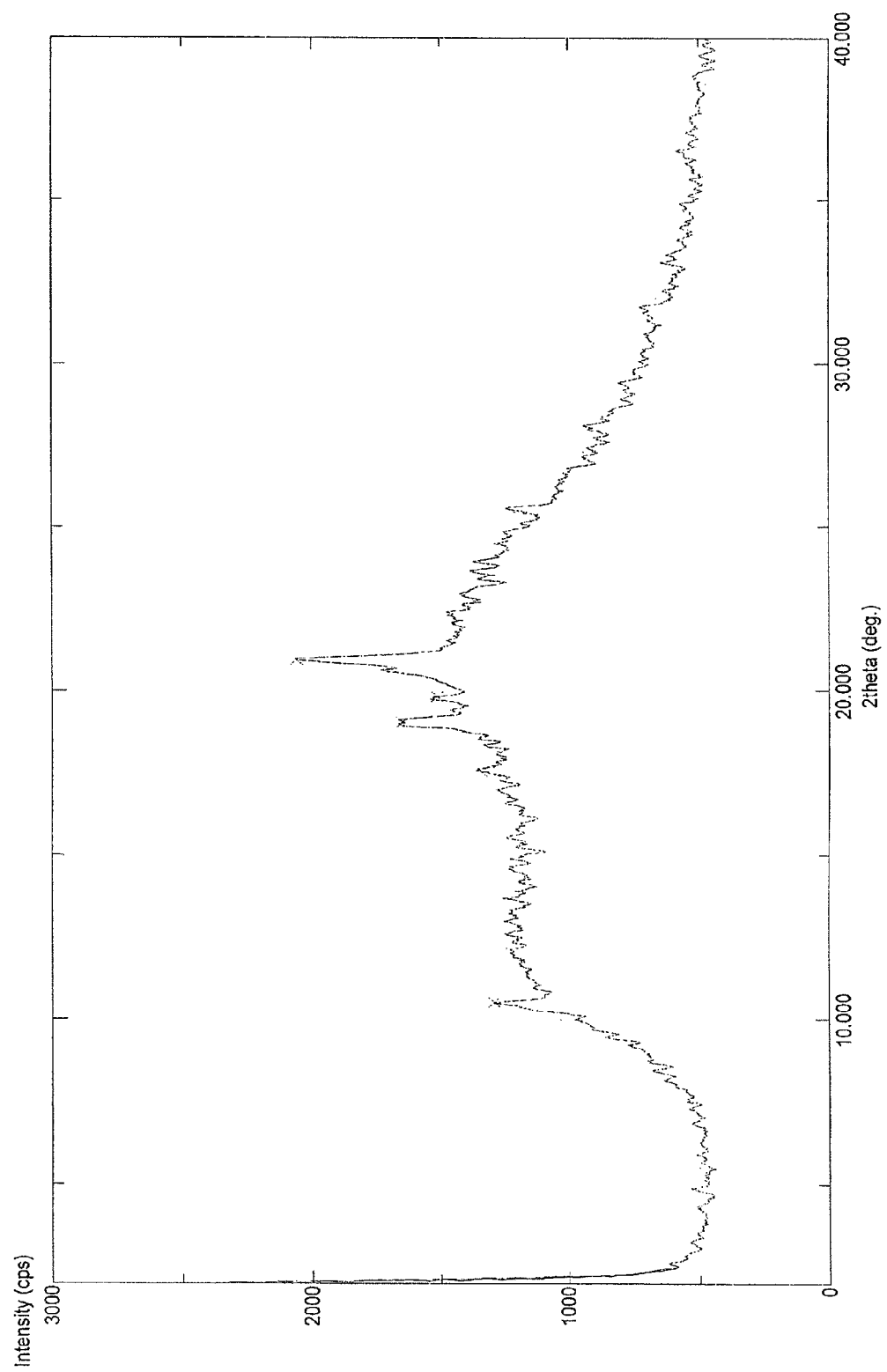

FIG. 6 discloses the x-ray diffractogram (XRD) of the amorphous form of dasatinib as per example-7.

Figure 7:
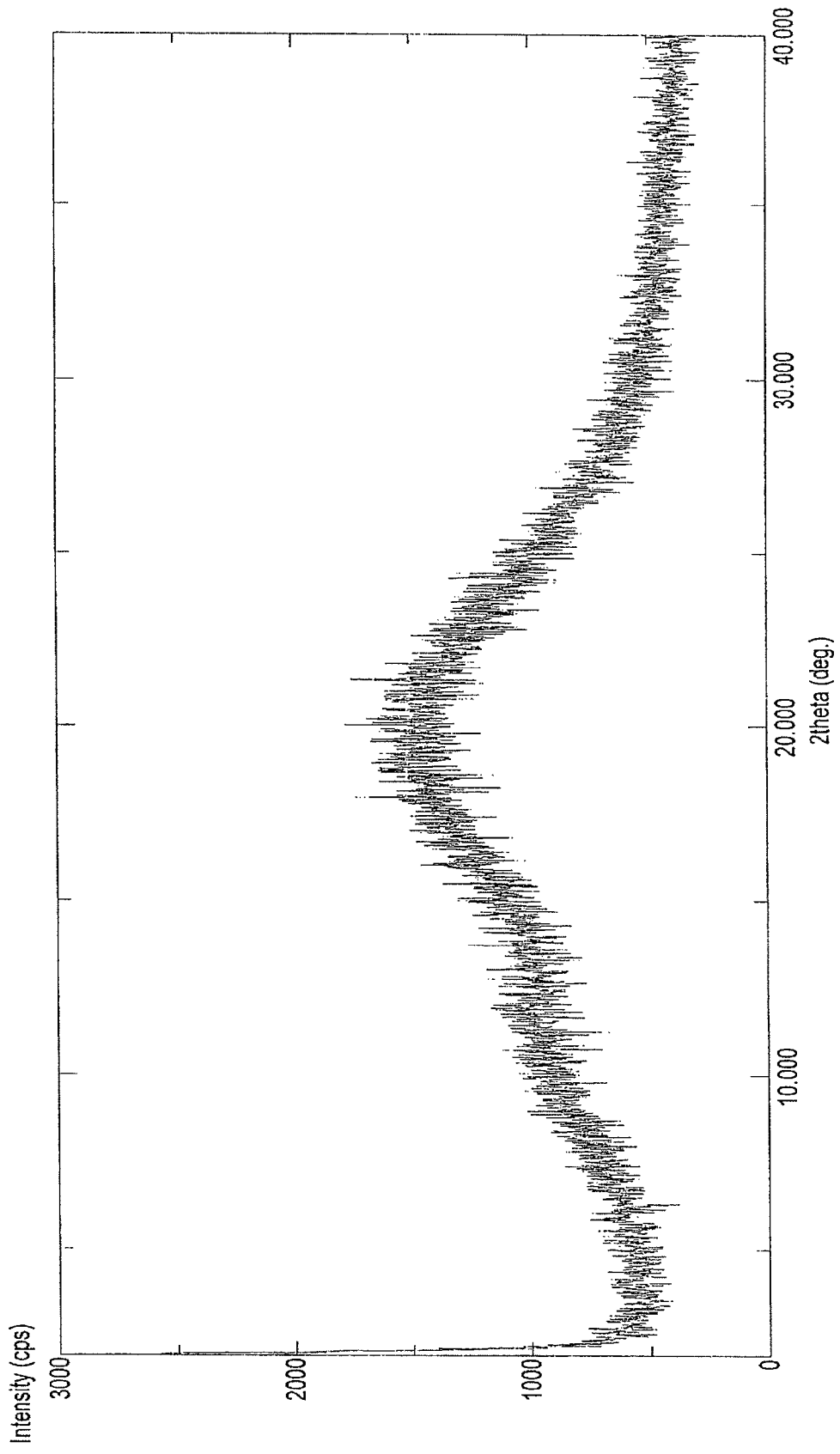

FIG. 7 discloses the x-ray diffractogram (XRD) of the amorphous form of dasatinib as per example-8.

Figure 8:
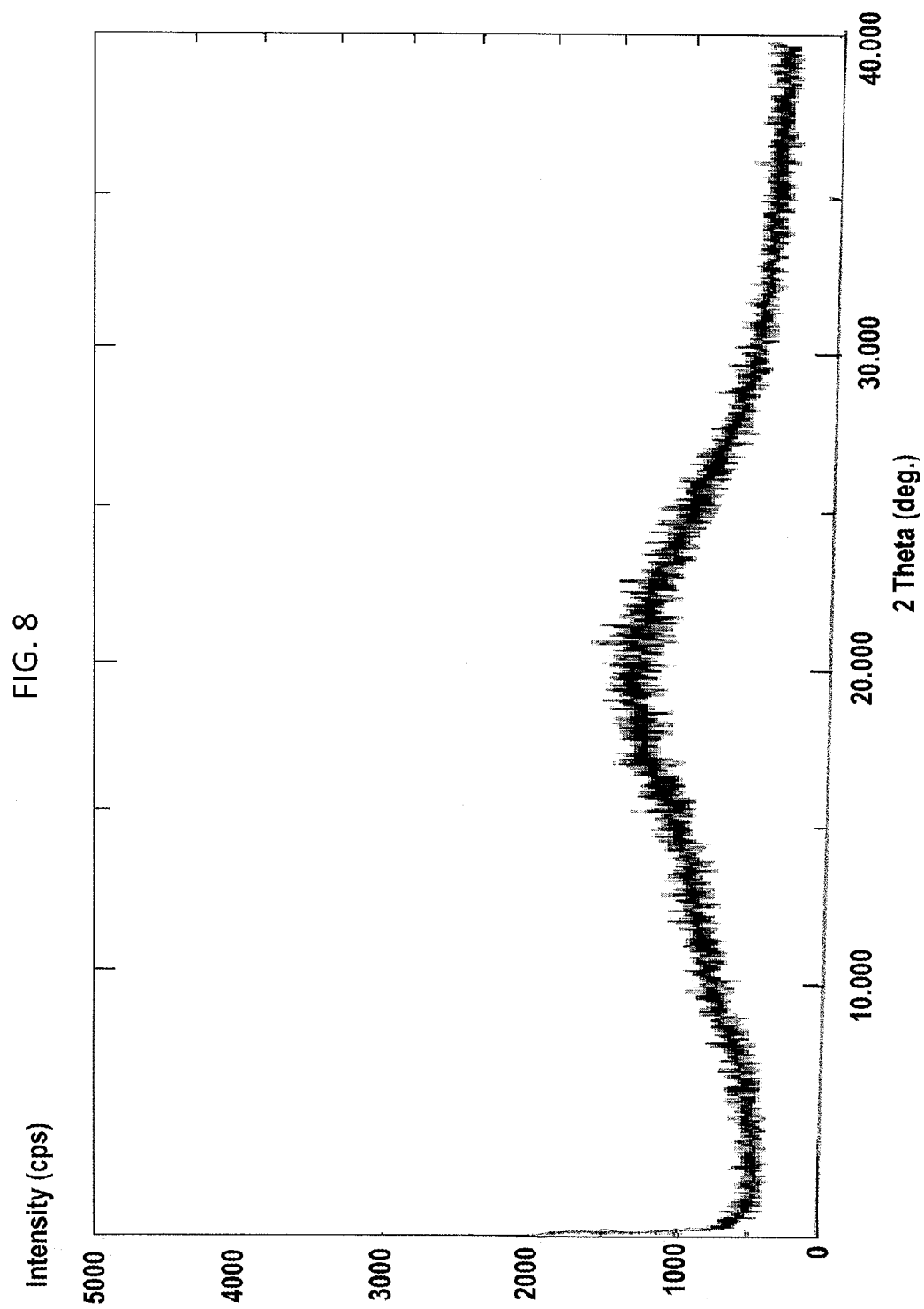

FIG. 8 discloses the x-ray diffractogram (XRD) of the amorphous form of dasatinib as per example-15.

Figure 9:
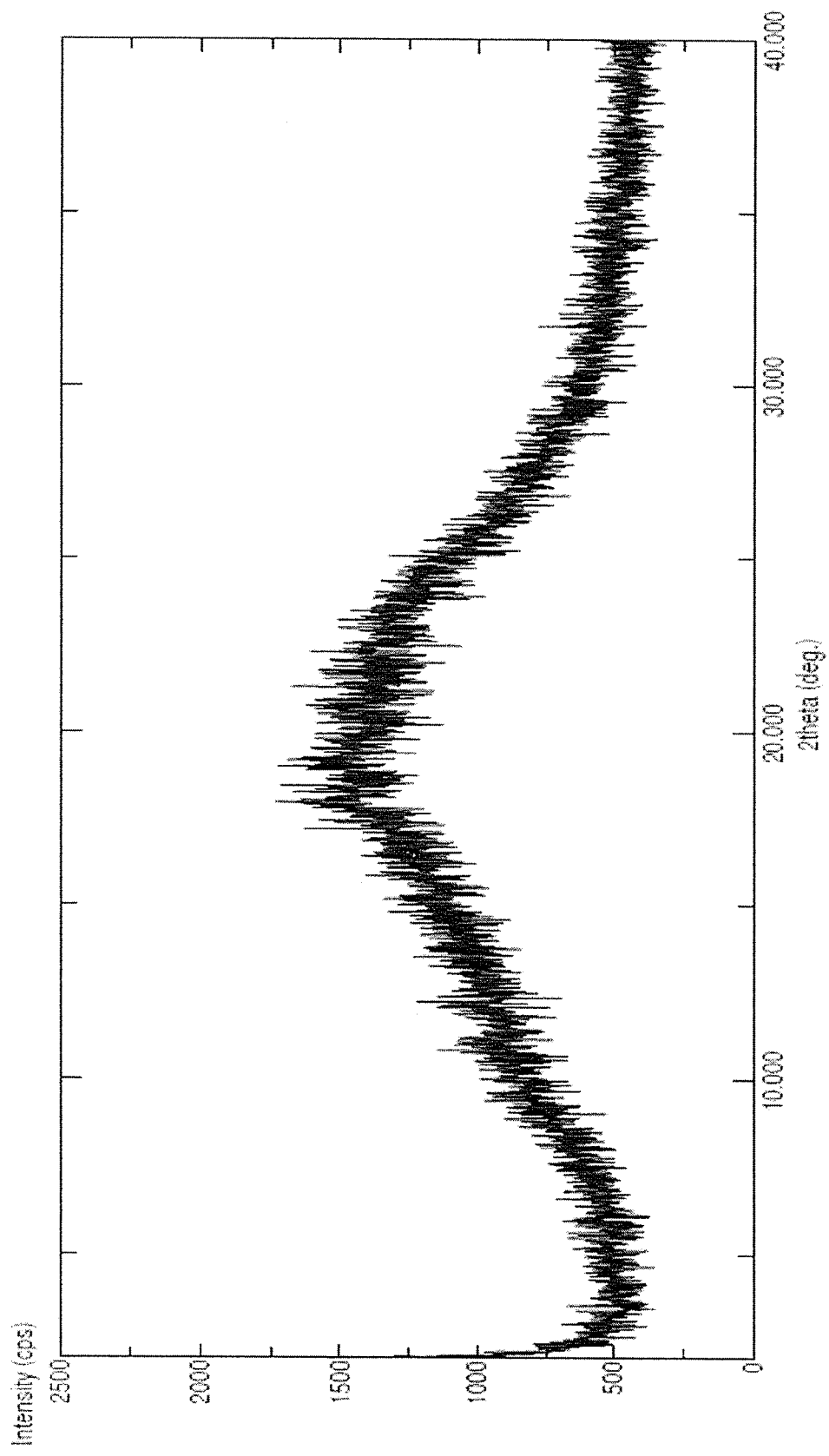

FIG. 9 discloses the x-ray diffractogram (XRD) of the amorphous form of dasatinib as per example-16.

Figure 10:
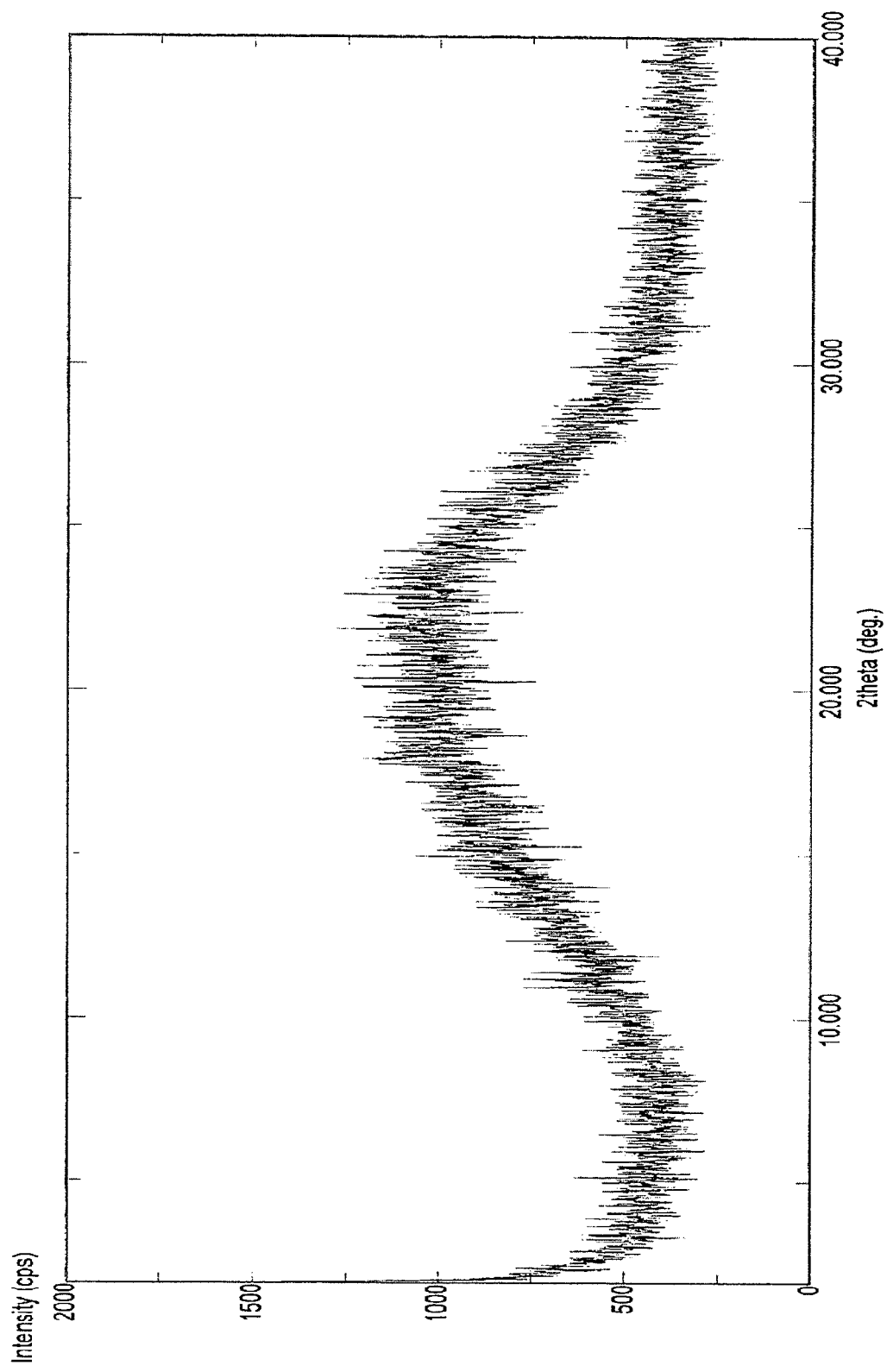

FIG. 10 discloses the x-ray diffractogram (XRD) of the amorphous form of dasatinib as per example-18.

Figure 11:
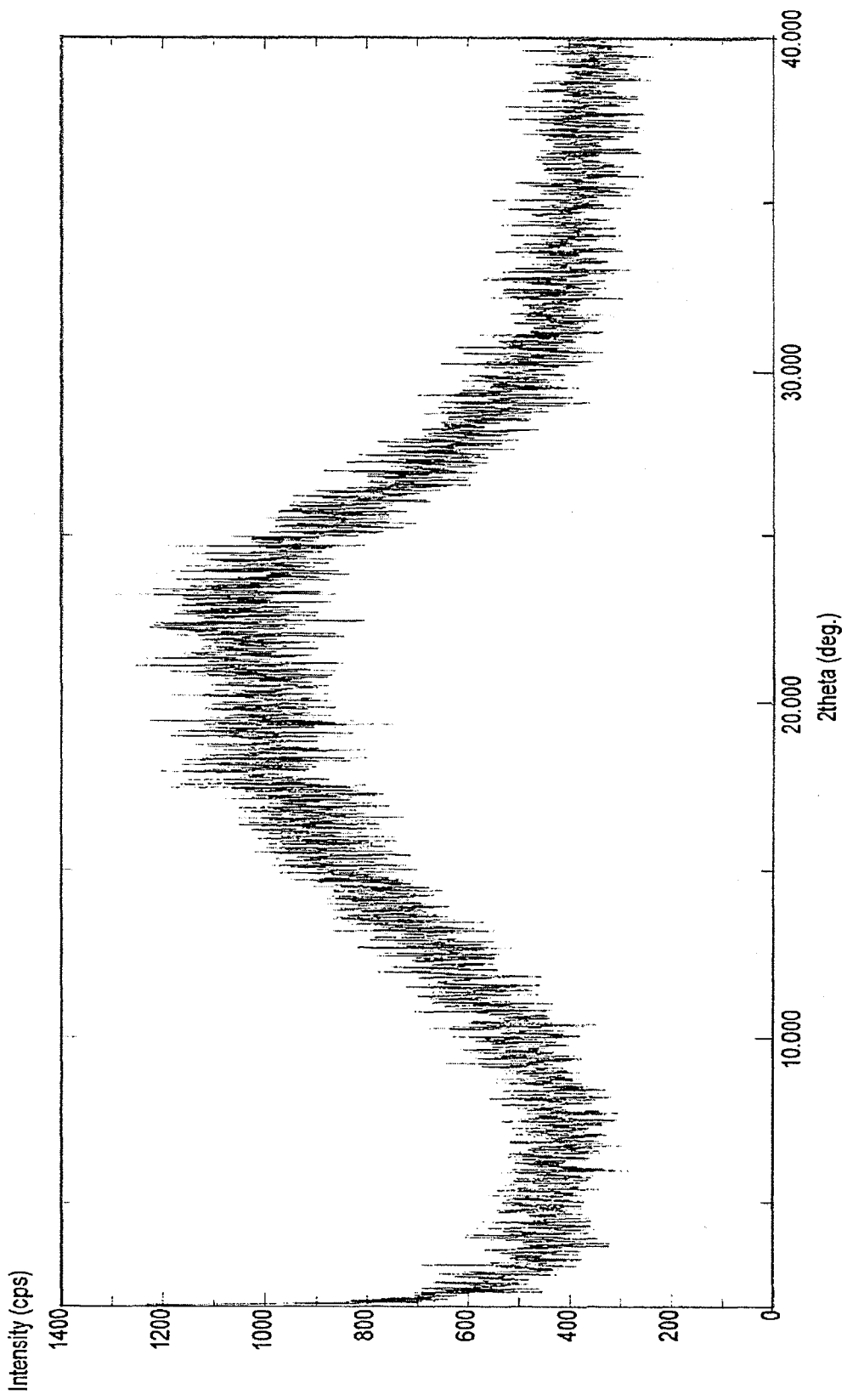

FIG. 11 discloses the x-ray diffractogram (XRD) of the amorphous form of dasatinib as per example-19.

Figure 12:
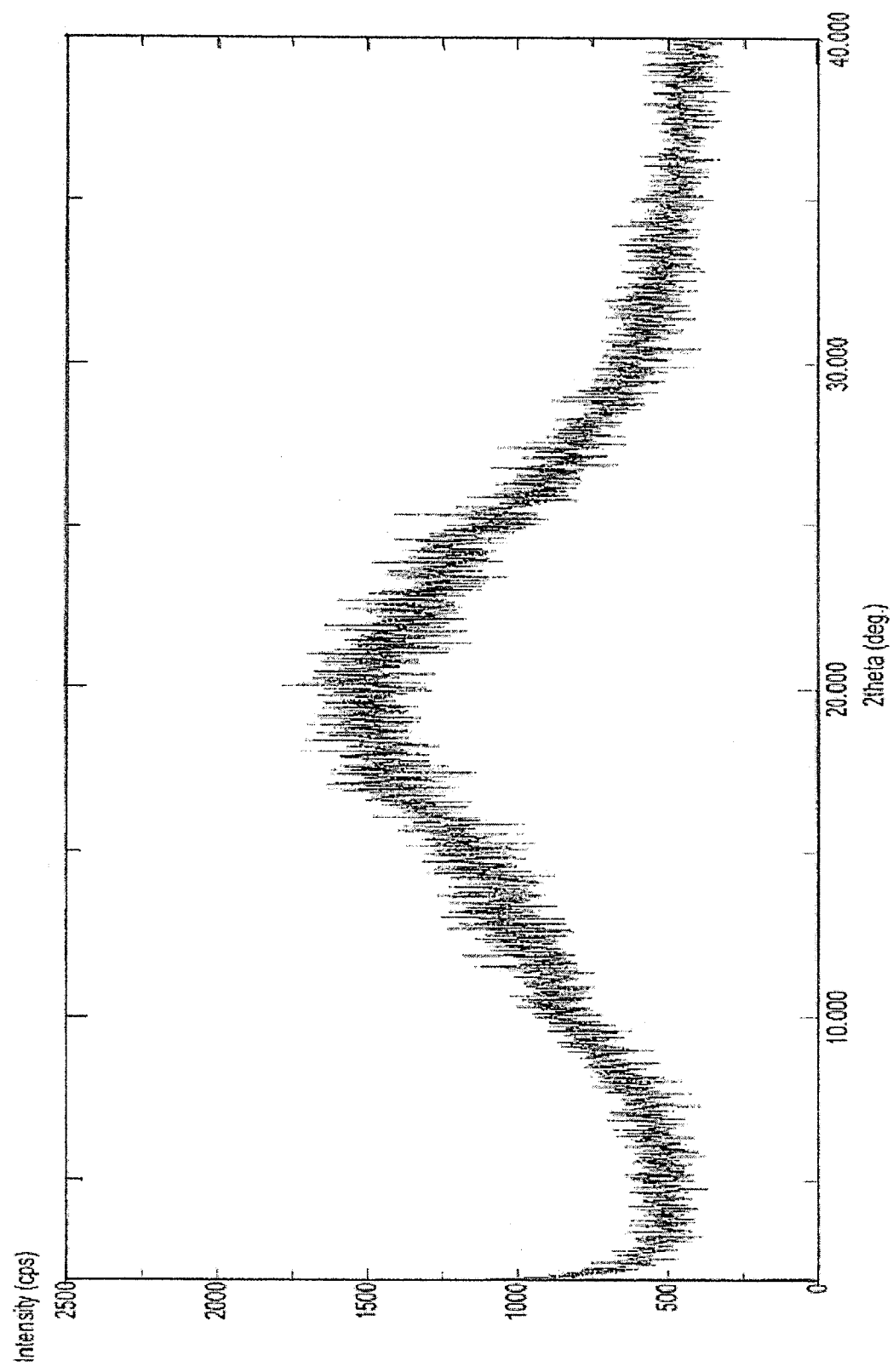

FIG. 12 discloses the x-ray diffractogram (XRD) of the amorphous form of dasatinib as per example-26.

DETAILED DESCRIPTION OF THE INVENTION

The above and other objects of the present invention are achieved by the process of the present invention, which leads to amorphous dasatinib suitable for pharmaceutical use and having greater stability. The invention provides a process for preparing amorphous form of dasatinib in a suitable organic solvent.

Optionally, the solution, prior to any solids formation, can be filtered to remove any undissolved solids, solid impurities and the like prior to removal of the solvent. Any filtration system and filtration techniques known in the art can be used.

All ranges recited herein include the endpoints, including those that recite a range "between" two values. Terms such as "about", "generally", "substantially," and the like are to be construed as modifying a term or value such that it is not an absolute. This includes, at very least, the degree of expected experimental error, technique error and instrument error for a given technique used to measure a value.

As used herein, the term "stable dasatinib" includes either: amorphous dasatinib that after exposure to a relative humidity of 75% at 40° C. or 60% at 25° C., for a period of at least three months contains less than about 0.5% (wt/wt) total impurities and doesn't change to crystalline form.

As used herein, the term "solid dispersion" means any solid composition having at least two components. In certain embodiments, a solid dispersion as disclosed herein includes an active ingredient dasatinib dispersed among at least one other component, for example a polymer.

The term "immobilize" as used herein with reference to the immobilization of the active compound i.e. dasatinib in the polymer matrix, means that molecules of the active compound interact with molecules of the polymer in such a way that the molecules of the dasatinib are held in the aforementioned matrix and prevented from crystal nucleation due to lack of mobility.

"Suitable solvent" means a single or a combination of two or more solvents.

As used herein, the term "controlled humidity" refers to a relative humidity in the range of 50±10%. In particular, the controlled humidity includes grinding process performed under controlled humidity followed by drying under controlled humidity for the preparation of dasatinib amorphous form.

As used herein, the term "grinder" includes mixers, mills, blenders, micronizers, and the like or a combination thereof. The terms "grinding", "milling", "mixing", "blending" and the like are interchangeable for achieving the homogeneous solid-solid mixture.

As used herein, the term "ball milling" as used herein means a process wherein shear forces are applied to a starting material by means of so-called milling balls located in a milling vessel. Typically and preferably, the milling vessel is rotated, wherein the milling balls collide with each other and with the API particles provided as the starting material. The ball mill preferred, may be planetary ball mill with model No. PM 100 and make of Retsch, Germany or make of Sisco India using balls of different size in combination.

In one general aspect, a solid-solid mixture of dasatinib of Formula (I), HPMC-AS or any such polymer may be milled by grinding action between two surfaces. Such milling has been traditionally carried out in pharmacy practice by compounding using a pestle and mortar or a common mixer grinder. According to the invention milling machines that work on substantially the same principle may be used in the present process. Examples of such milling machines include various makes of ball mills, roller mills, gyratory mills, multi-mills, Jet-mills, and the like.

In one more aspect, a mill such as a Micros Super Fine Mill (available from Nara Machinery Co. Ltd or Tokyo, Japan), Multi-Mill Sr. No. G. 1.1 32 (available from Grooves International Pharmaceutical & Chemical Machinery), Jet-Mill from Midas Micronizer M-100 Aerosol (No. 154/07-08 (available from microtech Enginering Company) or a common mixer grinder can be used. Alternatively another commercially available milling machine can be used.

The process parameter includes adding a solid-solid mixture of dasatinib and HPMC-AS in a grinder. A specific grinder used can be small-scale to large-scale mixer grinder which can easily prepare the homogeneous mixture of two solids. For example purpose, Quadro dry mixing apparatus for providing lump-free homogenous blending to ensure proper mixing. The varieties of mills and mixers provided in Perry's Chemical Engineers Handbook Seventh Edition by Robert H. Perry and Don W. Green can be used based on suitability are incorporated herein by reference in its entirety.

This grinding apparatus may consists of a water cooled jacketed bowl with the inside surface made of a suitable material such as Zirconium oxide, stainless steel, tungsten carbide, or aluminum oxide. Depending on the size of the grinder, the speed of rotation of the main shaft and the effective volume of the grinding chamber may vary. The effective volume of the grinding chamber may be in the range from about 0.45 liters to about 30 liters. For low capacity mills (such as 0, capacity 0.45 liters; or 5, capacity 4.8 liters), the speed of rotation of the main shaft is typically in the range from about 50 rpm to about 2000 rpm or higher depending upon the apparatus and volume.

In general aspect, the grinder may be a typical milling apparatus. This milling apparatus may be typically charged with feed material such that from about 10% to 30% of the effective volume of the grinding chamber is occupied. Examples of methods of transferring materials well known in the art include manual transfer, gravity feed, pneumatic conveying (using a high velocity air stream), and vacuum transfer. Such methods, well known in the art, may be used with the process of this invention to charge the feed material into the grinding volume available between the bowl and the sub-shafts. For obtaining homogeneous solid-solid mixture, the dasatinib of Formula (I) and HPMC-AS may be mixed in a wide range of ratios.

The period of milling using the mill may vary depending on the size of the mill, the speed of rotation of the main shaft, the type of feed material, and the quantity of feed material. The effects of these variables are well known in the art and the invention may be worked over a range of these variables. Typically, the period of milling ranges from about 15 minutes to 300 minutes.

According to another aspect of the invention, the dasatinib is subjected to grinding involving attrition of the particles and machine surfaces.

In one general aspect, there is provided a composition comprising an amorphous form of dasatinib of Formula (I). In particular, the composition is a solid dispersion that includes dasatinib of Formula (I)

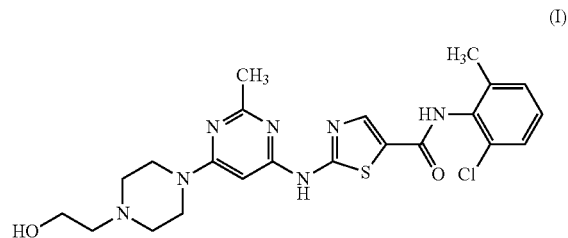 [SMILES: Cc1nc(Nc2ncc(C(=O)Nc3c(C)cccc3Cl)s2)cc(N2CCN(CCO)CC2)n1]

and a polymer.

In general, the polymer may be a non-ionic polymer or an ionic polymer. The polymer comprises of hydroxypropylmethyl cellulose acetate succinate (HPMC-AS), hydroxypropylmethyl cellulose (HPMC), methacrylic acid copolymers, polyvinylpyrrolidone (PVP) and the like. In particular, PVP of different grades like K-15, K-30, K-60, K-90 and K-120 may be used for the preparation of amorphous composition. More particular, hydroxypropylmethyl cellulose acetate succinate (HPMC-AS) and PVP K-30 may be used.

In some embodiments, the dasatinib of Formula (I) may be dispersed within a matrix formed by a polymer in its solid state such that it is immobilized in its amorphous form. The polymer may prevent intramolecular hydrogen bonding or weak dispersion forces between two or more drug molecules of dasatinib. The solid dispersion provides for a large surface area, thus further allowing for improved dissolution and bioavailability of dasatinib.

In some embodiments, the ratio of the amount of weight of dasatinib of Formula (I) within the solid dispersion to the amount by weight of the polymer therein is from about 1:1 to about 1:10. The composition of dasatinib with polymer, preferably PVP K-30 or HPMC-AS may be prepared by using about 1:1 to about 1:10 polymers with respect to dasatinib. The usage of higher molar amount of polymer increases the amorphous character of the drug substance.

In general, the amorphous solid dispersion is prepared by the process comprising grinding solid-solid mixture of dasatinib of Formula (I) and a polymer in a grinder.

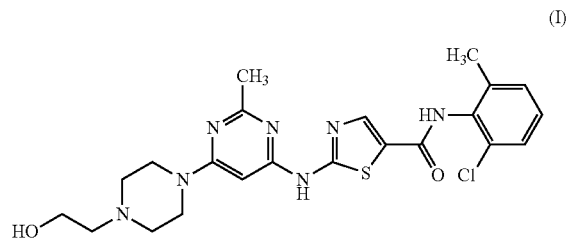 [SMILES: Cc1nc(Nc2ncc(C(=O)Nc3c(C)cccc3Cl)s2)cc(N2CCN(CCO)CC2)n1]

In some embodiments, the dasatinib of Formula (I) may be prepared as amorphous form by milling for sufficient time in absence of pharmaceutically acceptable carriers or polymers like PVP K-30 and HPMC-AS.

In some embodiments, the dispersion may also be prepared in presence of acidulant. The acidulant herein refers to citric acid hydrate.

In another general aspect there is provide a process for the preparation of dispersion of amorphous dasatinib of Formula (I) having at least one polymer, the process comprising mixing dasatinib of Formula (I) with a polymer in a suitable organic solvent and obtaining amorphous dispersion of dasatinib by removal of solvent.

The compound dasatinib of Formula (I) and a polymer (for example HPMC-AS or PVP K-30) may be dissolved in a suitable organic solvent comprises one or more of low boiling solvents like methanol, ethanol, isopropanol, acetone, ethyl acetate and the like or mixture thereof with water. The amorphous solid dispersion may be obtained by removal of solvent (for example by evaporation, evaporation under reduced pressure, spray drying, lyophilization, flash evaporation, vacuum distillation and the like) thereby leaving the amorphous solid dispersion precipitated in a matrix formed by the polymer.

In another general aspect, there is provided an amorphous form of dasatinib of Formula (I) substantially free from residual solvents.

In another general embodiment, there is provided a process for preparation an amorphous form of dasatinib, which includes one or more of the following steps:
a) providing a solution of dasatinib composition in one or more of suitable solvent or mixture thereof; and
b) obtaining an amorphous form of dasatinib by removal of solvent.

Step a) involves providing a solution of dasatinib composition in one or more of solvent or mixture thereof.

The solution for step a) can be obtained by the known methods that include:
i. direct use of a reaction mixture containing dasatinib that is obtained in the course of its synthesis; or
ii. dissolving dasatinib and a polymer optionally in presence of acidulant in one or more of suitable solvent or mixture thereof.

Suitable solvents that may be used in step a) include but are not limited to one or more of alcohols such as methanol, ethanol, isopropanol, 2-propanol, 1-butanol, t-butyl alcohol, and the like; ketones such as acetone, butanone, methyl isobutyl ketone, and the like; esters such as ethyl acetate, isopropyl acetate, t-butyl acetate, isobutyl acetate, chlorinated hydrocarbons such as methylene dichloride, ethylene dichloride, chlorobenzene, and the like, nitriles like acetonitrile, and polar aprotic solvents like N,N-dimethylformamide, N,N-dimethylacetamide, N-methyl pyrrolidone, dimethylsulfoxide, and mixtures thereof.

Step b) involves isolation of an amorphous form of dasatinib from the solution of step a). The isolation may be affected by removing the solvent. Suitable techniques which may be used for the removal of solvent include using a rotational distillation device such as a Buchi Rotavapor, spray drying, agitated thin film drying ("ATFD"), freeze drying (lyophilization), and the like or any other suitable technique.

Alternatively, isolation can be effected by addition of suitable antisolvent to the solution obtain in step a), optionally by concentrating the solution obtained in step a). Suitable antisolvents that may be used can be selected from one or more of hydrocarbons like hexanes, n-heptane, n-pentane, cyclohexane, methylcyclohexane and the like; aromatic hydrocarbons like toluene, xylene, ethylbenzene and the like; ethers like diethyl ether, diisopropyl ether, t-butyl methyl ether, dibutyl ether, tetrahydrofuran, 1,4-dioxane, 2-methoxyethanol and the like.

In one preferred aspect, there is provided spray drying a solution of dasatinib composition that involves the spray drying of feed stock, which is prepared as discussed below, wherein any crystalline form of dasatinib may be used. The feed stock is dozed into the spray-drying instrument JISL Mini Spray-drier LSD-48 and spray drying is carried out under the following parameters.

| Sr. No. | Parameters | Conditions |
|---|---|---|
| a) | Feed pump | 10-50 rpm |
| b) | Inlet temperature | 35°-80° C. |
| c) | Outlet temperature | 30°-60° C. |
| d) | Aspirator rate | 1000-1500 rpm |
| e) | Vacuum for conveying the dry product | 30-120 mm of Hg |
| f) | Hot air supply | 2-4 Kg/cm$^2$ |
| g) | Atomizer Speed: | 40,000-100,000 rpm |

In the present invention, feed stock of dasatinib composition is conveniently prepared by dissolving any known forms or wet cake of dasatinib alongwith a polymer in the solvent comprises one or more of acetone, $C_{1-4}$ alcohol, $C_{2-6}$ acetate, acetonitrile, methylene dichloride, water or mixture thereof. In particular, methanol, ethanol, acetone, ethyl acetate, methylene dichloride, water-methanol or water-ethanol, water-acetone are suitable solvent used or such solvents that evaporate easily to afford dry product, most particularly acetone, methanol, ethanol, ethyl acetate or mixtures thereof with water may be used.

In another preferred feature, the spray drying of dasatinib composition may be performed by a) maintaining the feed rate of the feed stock at 50-250 ml/hr, preferably 100-200 ml/hr; b) maintaining the inlet temperature in the range of 35° C.-80° C., preferably, 50° C.-70° C.; c) maintaining the aspirator rate between 1000-1500 rpm, preferably 1200-1400 rpm; d) maintaining the outlet temperature in the range of 30° C. to 60° C., preferably, 40° C. to 50° C.; e) maintaining air flow at 2-4 Kg/cm$^2$, preferably 2 Kg/cm$^2$; f) maintaining Atomizer speed between 20,000-100,000 rpm, preferably, 40,000-50,000 rpm, and; g) maintaining the vacuum at 30-120 mm of Hg, preferably 50-80 mm of Hg.

In another general aspect, there is provided a stable amorphous form of dasatinib of Formula (I), which is at least stable during storage and drying.

In one more aspect, the inventors also have developed a process for the preparation of the amorphous form of dasatinib of Formula (I) by adding a solid-solid mixture of dasatinib and HPMC-AS in a grinder and grinding the solid-solid mixture to obtain the amorphous form of dasatinib.

In another general aspect of the invention, there is provided a process for preparation of the amorphous form of dasatinib, by adding a solid-solid mixture of dasatinib and HPMC-AS in a grinder and grinding the solid-solid mixture under controlled humidity to obtain the amorphous form of dasatinib.

In another general aspect, there is provided an amorphous form of dasatinib of Formula (I) substantially free from of residual solvents.

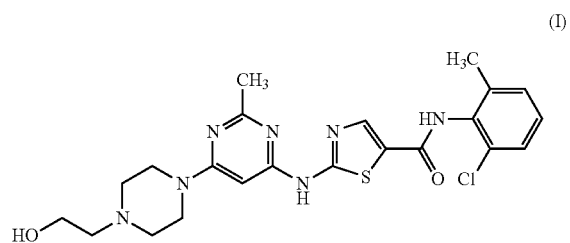 [SMILES: Cc1nc(Nc2ncc(C(=O)Nc3c(C)cccc3Cl)s2)cc(N2CCN(CCO)CC2)n1]

In further aspect, the stable amorphous dasatinib, can be stored under nitrogen atmosphere and packed in a double polythene bag tied with a thread, keeping primary packing containing amorphous dasatinib inside a black color polyethylene bag containing oxygen busters and sealing it, placing above the double polyethylene bag inside a triple laminated bag optionally containing oxygen busters and sealing it, and placing the sealed triple laminated bag inside a closed high density polyethylene (HDPE) container and storing in controlled environment chamber at about 25° C. and/or 40° C.

In another general aspect, there is provided an amorphous form of dasatinib of Formula (I) having HPLC purity greater than about 95%, or greater than about 98%, or greater than about 99%, or greater than about 99.5%, or greater than about 99.8%, or greater than about 99.9%, as determined using high performance liquid chromatography (HPLC).

In another general aspect, there is provided a pharmaceutical composition comprising an amorphous form of dasatinib of Formula (I) substantially free residual solvents as measured by GC together with one or more pharmaceutically acceptable carriers, excipients or diluents.

In another general aspect, there is provided a pharmaceutical composition comprising an amorphous form of dasatinib of Formula (I) substantially free from crystalline forms together with one or more pharmaceutically acceptable carriers, excipients or diluents.

In another general aspect, there is provided pharmaceutical composition comprising therapeutically effective amount of an amorphous dasatinib having at least one polymer together one or more of pharmaceutically acceptable carriers, excipients or diluents.

In another general aspect, there is provided amorphous form of dasatinib having particle size distributions wherein the 10th volume percentile particle size (D10) is less than about 50 µm, the 50th volume percentile particle size (D50) is less than about 200 µm, or the 90th volume percentile particle size (D90) is less than about 400 µm, or any combination thereof.

In further aspect, the dasatinib may be micronized to achieve the better particle size distribution in order to make suitable Formulation.

The active ingredient may be micronized prior to compression and shearing. Micronisation may be by any suitable method. Micronization is the process of reducing the average diameter of solid material particles, for example by milling or grinding. In one aspect a micronized active is an active ingredient that has been subjected to a mechanical process which applies sufficient force to the active ingredient that the process is capable of breaking coarse particles down to fine particles.

In one aspect micronization of the active ingredient may be achieved using one or a combination of the following methods: ball milling, jet milling, jet blending, high-pressure homogenation, or any other milling method.

Ball milling is a milling method used in many of the prior art co-milling processes. Centrifugal and planetary ball milling may also be used.

Jet mills are capable of reducing solids to particle sizes in the low-micron to submicron range. The grinding energy is created by gas streams from horizontal grinding air nozzles. Particles in the fluidised bed created by the gas streams are accelerated towards the centre of the mill, colliding within. The gas streams and the particles carried in them create a violent turbulence and, as the particles collide with one another, they are pulverized.

Alternatively micronized active ingredient may be produced by using a high energy media mill or an agitator bead mill, for example, the Netzsch high energy media mill, or the DYNO-mill (Willy A. Bachofen A G, Switzerland).

Powder X-ray Diffraction of amorphous dasatinib can be obtained under following conditions.

Powder X-ray Diffraction: X-ray powder diffraction spectrum was observed on a MF 2100 2KW X-ray Powder diffractometer of make Rigaku or any equivalent, having a Copper K$\alpha$-radiation at a voltage of 40 kV and 30 mA. Approximately 150 mg sample was gently flattened on a quartz plate without further processing (e.g. Grinding and sieving) and scanned from 4° to 40° at 0.010° sampling width and 4.000° per minute.

According to another aspect, dasatinib to be used as the starting material may be prepared by the known methods reported in the prior i.e. by using the process as per U.S. Pat. No. 6,596,746 B1 or U.S. Pat. No. 7,491,725 B2, which is incorporated herein as reference.

The invention also encompasses pharmaceutical compositions comprising dasatinib of the invention. As used herein, the term "pharmaceutical compositions" includes pharmaceutical formulations like tablets, pills, powders, liquids, suspensions, emulsions, granules, capsules, suppositories, or injection preparations.

Pharmaceutical compositions containing the dasatinib of the invention may be prepared by using diluents or excipients such as fillers, bulking agents, binders, wetting agents, disintegrating agents, surface active agents, and lubricants. Various modes of administration of the pharmaceutical compositions of the invention can be selected depending on the therapeutic purpose, for example tablets, pills, powders, liquids, suspensions, emulsions, granules, capsules, suppositories, or injection preparations.

In another general aspect, there is provided a pharmaceutical composition comprising therapeutically effective amount of storage stable amorphous form of dasatinib substantially free from crystalline form together with one or more pharmaceutically acceptable carriers, excipients or diluents.

In another general aspect, there is provided a pharmaceutical composition comprising a stabilized amorphous solid dispersion of dasatinib of Formula (I) together with one or more pharmaceutically acceptable carrier, optionally with one or more pharmaceutically acceptable excipients.

The present invention is further illustrated by the following example which is provided merely to be exemplary of the invention and do not limit the scope of the invention. Certain modification and equivalents will be apparent to those skilled in the art and are intended to be included within the scope of the present invention.

EXAMPLES

Reference Example 1

Preparation of Amorphous Dasatinib as per Example-26 of U.S. Pat. No. 7,973,045 B2

In 100 ml three necked round bottom flask equipped with mechanical stirrer, thermometer and an addition funnel, dasatinib (592 mg, 1.49 mmol), piperazine ethanol (391 mg, 3 mmol) and N,N-diisopropylethyl amine (0.52 ml, 3 mmol) were added in dimethylformamide (2.5 ml, 2.5 V). The reaction mixture was heated at 90° C. under stirring for 2.5 hour. The reaction mixture was cooled to 0 to 5° C. and 20 ml water was added and stirred for 1 hour. The product was filtered under suction, washed with water and suck dried for 1 hour to obtain the amorphous form of dasatinib. (FIG. 1: XRD) and (FIG. 2: TGA).

Example 1

Preparation of Amorphous Dasatinib

In 100 ml three necked round bottom flask equipped with mechanical stirrer, thermometer and an addition funnel, dasatinib (0.5 gm, 1.02 mmol), PVP K-30 (4 gm, 8 times) and 88% methanol in water (12.5 ml, 25V) were heated to 65-70° C. to get clear solution. The reaction mixture was stirred for 1 hour, concentrated under vacuum (1.5 mbar) at 65-70° C. and degassed under vacuum (1.5 mbar) for 1 hour at 70° C. to obtain the title compound in substantially pure amorphous form. (FIG. 3: XRD).

Example 2

Preparation of Amorphous Dasatinib

In 100 ml three necked round bottom flask equipped with mechanical stirrer, thermometer and an addition funnel, dasatinib (0.5 gm, 1.02 mmol), PVP K-30 (1 gm, 2 times), citric acid hydrate (0.1 gm, 20%) and 88% methanol in water (12.5 ml, 25V) were heated at 65-70° C. to get clear solution. The reaction mixture was stirred for 1 hour, concentrated under vacuum (1.5 mbar) at 65-70° C. and degassed under vacuum (1.5 mbar) for 1 hour at 70° C. to obtain the title compound in substantially pure amorphous form. (FIG. 4: XRD).

Example 3

Preparation of Amorphous Dasatinib

In 100 ml three necked round bottom flask equipped with mechanical stirrer, thermometer and an addition funnel, dasatinib (0.5 gm, 1.02 mmol), PVP K-30 (1 gm, 2 times) and citric acid hydrate (0.1 gm, 20%) in 88% methanol in water (12.5 ml, 25V) were heated at 65 to 70° C. to get clear solution. The reaction mixture was stirred for 2 hours, concentrated under vacuum (1.5 mbar) at 70° C. and degassed under vacuum (1.5 mbar) for 1 hr at 70° C. to obtain the title compound in substantially pure amorphous form.

Example 4

Preparation of Amorphous Dasatinib

In 100 ml three necked round bottom flask equipped with mechanical stirrer, thermometer and an addition funnel, dasatinib (0.5 gm, 1.02 mmol), PVP K-30 (2 gm, 4 times) and 88% methanol in water (10 ml, 20V) were heated at 65-70° C. to get clear solution. The reaction mixture was stirred for 2 hours and 15 mL methylterbutylether was added. The reaction mixture was concentrated under vacuum (1.5 mbar) at 65-70° C. and degassed under vacuum (1.5 mbar) for 1 hour at 65° C. to obtain the title compound in substantially pure amorphous form. (FIG. 5: XRD)

Example 5

Preparation of Amorphous Dasatinib

In 100 ml three necked round bottom flask equipped with mechanical stirrer, thermometer and an addition funnel, dasatinib (0.3 gm, 0.614 mmol), PVP K-30 (1.2 gm, 4 times) in methanol (12 ml, 40V) were heated at 65-70° C. to get clear solution. The reaction mixture was stirred for 2 hours and concentrated under vacuum at 65-70° C. 12 ml diethyl ether was added to obtain clear reaction mixture and concentrated under vacuum (1.5 mbar) at 35-40° C. and degassed under vacuum (1.5 mbar) for 1 hour at 40° C. to obtain the title compound in substantially pure amorphous form.

Example 6

Preparation of Amorphous Dasatinib

In 100 ml three necked round bottom flask equipped with mechanical stirrer, thermometer and an addition funnel, dasatinib (0.5 gm, 1.02 mmol), PVP K-30 (2 gm, 4 times) in mixture of methanol/diethyl ether (1:1) (17.6 ml, 35.2 V) were heated at 60° C. to get clear solution. The reaction mixture was stirred for 2 hour, concentrated under vacuum (1.5 mbar) at 60° C. and degassed under vacuum (1.5 mbar) for 1 hour at 60° C. to obtain the title compound in substantially pure amorphous form.

Example 7

Preparation of Amorphous Dasatinib

In 100 ml three necked round bottom flask equipped with mechanical stirrer, thermometer and an addition funnel, dasatinib (2 gm, 4.1 mmol) and PVP K-30 (4 gm, 2 times) were grinded in grinding bowl by using planetary ball milling (1 hour milling by 10 min interval every 15 min grinding at RPM 200). Further, the same material mixed in grinding bowl by using planetary ball milling (1 hr milling by 10 min interval every 15 min grinding at RPM 200) to obtain the title compound in substantially pure amorphous form. (FIG. 6: XRD). The obtained product contains residual solvent well within ICH limit having HPLC purity 99.8%.

Example 8

Preparation of Amorphous Dasatinib

In 100 ml three necked round bottom flask equipped with mechanical stirrer, thermometer and an addition funnel, dasatinib (0.5 gm, 1.02 mmol), Hydroxypropylmethyl cellulose Acetate Succinate HPMC-AS (1 gm, 2 times) and 90% ethanol in water (15 ml, 30V) were heated at 65-70° C. to get clear solution. The reaction mixture was stirred for 2 hour and concentrated under vacuum (1.5 mbar) at 70° C. and degassed under vacuum (1.5 mbar) for 1 hour at 70° C. to obtain the title compound in substantially pure amorphous form. (FIG. 7: XRD). The obtained product contains residual solvent well within ICH limit having HPLC purity 99.9%.

Example 9

Preparation of Amorphous Dasatinib

In 100 ml three necked round bottom flask equipped with mechanical stirrer, thermometer and an addition funnel, dasatinib (0.5 gm, 1.02 mmol) in 88% methanol in H$_2$O (12.5 ml, 25V) were heated at 60° C. Hydroxypropylmethyl cellulose Acetate Succinate (HPMC-AS) (0.5 gm, 1 time) in acetone (7.5 ml, 15V) was taken in another flask and heated at 60° C. The dasatinib solution was added in HPMC-AS solution to obtain a clear reaction mixture, which was stirred for 2 hours and concentrated under vacuum (1.5 mbar) at 60° C. and degassed under vacuum (1.5 mbar) for 1 hour at 60° C. to obtain the title compound in substantially pure amorphous form.

Example 10

Preparation of Amorphous Dasatinib

In 100 ml three necked round bottom flask equipped with mechanical stirrer, thermometer and an addition funnel, dasatinib (0.5 gm, 1.02 mmol), HPMC-AS (0.5 gm, 1 time) and 90% ethanol in water (15 ml, 30V) were heated at 65-70° C. to get clear solution. The reaction mixture was stirred for 2 hours, concentrated under vacuum (1.5 mbar) at 70° C. and degassed under vacuum (1.5 mbar) for 1 hour at 70° C. to obtain the title compound in substantially pure amorphous form.

Example 11

Preparation of Amorphous Dasatinib

In 100 ml three necked round bottom flask equipped with mechanical stirrer, thermometer and an addition funnel, dasatinib (0.5 gm, 1.02 mmol), microcrystalline cellulose (MCC) (0.5 gm, 1 time) and of 88% methanol in water (17.6 ml, 35.2 V) were heated at 65-70° C. to get clear solution. The reaction mixture was stirred for 2 hours, concentrated under vacuum (1.5 mbar) at 65° C. and degassed under vacuum (1.5 mbar) for 1 hour at 65° C. to obtain the title compound in substantially pure amorphous form.

Example 12

Preparation of Amorphous Dasatinib

In 100 ml three necked round bottom flask equipped with mechanical stirrer, thermometer and an addition funnel, dasatinib (0.5 gm, 1.02 mmol), HPMC-AS (1 gm, 2 times) and citric acid hydrate (0.1 gm, 20%) in 90% ethanol in water (15 ml, 30V) were heated at 65 to 70° C. to get clear solution. The reaction mixture was stirred for 2 hours, concentrated under vacuum (1.5 mbar) at 70° C. and degassed under vacuum (1.5 mbar) for 1 hour at 70° C. to obtain the title compound in substantially pure amorphous form.

Example 13

Preparation of Amorphous Dasatinib

In 100 ml three necked round bottom flask equipped with mechanical stirrer, thermometer and an addition funnel, dasatinib (0.5 gm, 1.02 mmol), PVP K-30 (0.5 gm, 1 time) and citric acid hydrate (0.1 gm, 20%) in 88% methanol in water (12.5 ml, 25V) were heated at 65 to 70° C. to get clear solution. The reaction mixture was stirred for 2 hours, concentrated under vacuum (1.5 mbar) at 70° C. and degassed under vacuum (1.5 mbar) for 1 hour at 70° C. to obtain the title compound in substantially pure amorphous form.

Example 14

Preparation of Amorphous Dasatinib

In 100 ml three necked round bottom flask equipped with mechanical stirrer, thermometer and an addition funnel, dasatinib (0.5 gm, 1.02 mmol), HPMC-AS (0.5 gm, 1 time) and citric acid hydrate (0.1 gm, 20%) in 90% ethanol in water (15 ml, 30V) were heated at 65 to 70° C. to get clear solution. The reaction mixture was stirred for 2 hours, concentrated under vacuum (1.5 mbar) at 70° C. and degassed under vacuum (1.5 mbar) for 1 hour at 70° C. to obtain the title compound in substantially pure amorphous form.

Example-15

Preparation of Amorphous Dasatinib

Dasatinib (2 gm, 4.098 mmol) and HPMC-AS (2 gm, 1 time) were placed in 125 ml milling vessel of Planetary Ball Mill with 12 no's of tungsten carbide balls having diameter of 10 mm each, rotated for 2 hours at 200 rpm by using set time of 15 min every 10 min interval time, unloaded material to get 3.66 gm dasatinib amorphous form with 91.5% yield having HPLC purity 99.9%. The obtained product contains residual solvent well below ICH limit. (FIG. 8: XRD)

Example-16

Preparation of Amorphous Dasatinib

Dasatinib (5 gm, 10.24 mmol) was placed in 125 ml milling vessel of Planetary Ball Mill with 12 no's of tungsten carbide balls having diameter of 10 mm each, rotated for 2 hours at 200 rpm by using set time of 15 min every 10 min interval time, unloaded material to get 3.8 gm dasatinib amorphous form with 76% yield. (FIG. 9: XRD)

Example-17

Preparation of Amorphous Dasatinib

Dasatinib (5 gm, 10.24 mmol) was placed in 125 ml milling vessel of Planetary Ball Mill with 12 no's of tungsten carbide balls having diameter of 10 mm each, rotated for 4 hours at 200 rpm by using set time of 15 min every 10 min interval time, unloaded material to get 3.55 gm dasatinib amorphous form with 71% yield.

Example-18

Preparation of Amorphous Dasatinib

Dasatinib (5 gm, 10.24 mmol) was placed in 125 ml milling vessel of Planetary Ball Mill with 12 no's of tungsten carbide balls having diameter of 10 mm each, rotated for 6 hours at 200 rpm by using set time of 15 min every 10 min interval time, unloaded material to get 3.1 gm dasatinib amorphous form with 62% yield. (FIG. 10: XRD)

Example-19

Preparation of Amorphous Dasatinib

Dasatinib (5 gm, 10.24 mmol) was placed in 125 ml milling vessel of Planetary Ball Mill with 12 no's of tungsten carbide balls having diameter of 10 mm each, rotated for 8 hours at 200 rpm by using set time of 15 min every 10 min interval time, unloaded material to get 3 gm dasatinib amorphous form with 60% yield. (FIG. 11: XRD)

Example-20

Preparation of Amorphous Dasatinib

Dasatinib (5 gm, 10.24 mmol) was placed in 125 ml milling vessel of Planetary Ball Mill with 12 no's of tungsten carbide balls having diameter of 10 mm each, rotated for 4 hours at 100 rpm by using set time of 15 min every 10 min interval time, unloaded material to get 4.2 gm dasatinib amorphous form with 84% yield.

Example-21

Preparation of Amorphous Dasatinib

Dasatinib (5 gm, 10.24 mmol) was placed in 125 ml milling vessel of Planetary Ball Mill with 12 no's of tungsten carbide balls having diameter of 10 mm each, rotated for 4 hours at 400 rpm by using set time of 15 min every 10 min interval time, unloaded material to get 3.87 gm dasatinib amorphous form with 77.4% yield.

Example-22

Preparation of Amorphous Dasatinib

Dasatinib (5 gm, 10.24 mmol) was placed in 125 ml milling vessel of Planetary Ball Mill with 12 no's of tungsten carbide balls having diameter of 10 mm each, rotated for 4 hours at 650 rpm by using set time of 15 min every 10 min interval time, unloaded material to get 4.25 gm dasatinib amorphous form with 85% yield.

Example-23

Preparation of Amorphous Dasatinib

Dasatinib (5 gm, 10.24 mmol) and HPMC-AS (10 gm, 2 times) were placed in 125 ml milling vessel of Planetary Ball Mill with 4 no's of tungsten carbide balls having diameter of 20 mm each, rotated for 2 hours at 200 rpm by using set time of 15 min every 10 min interval time, unloaded material to get 14.57 gm dasatinib amorphous form with 97.13% yield.

Example-24

Preparation of Amorphous Dasatinib

Dasatinib (10 gm, 20.48 mmol), HPMC-AS (15 gm, 1.5 times) and Kollidon VA 64 (15 gm, 1.5 times) were placed in a grinding jar having volume of 500 ml of electronic mixer grinder, grinded the solid mixture for 1 hour at 12000-18000 rpm and unloaded material to get 32.5 gm dasatinib amorphous form with 81.25% yield.

Example-25

Preparation of Amorphous Dasatinib

In 100 ml three necked round bottom flask equipped with mechanical stirrer, thermometer and an addition funnel, dasatinib (0.5 gm, 1.02 mmol), HPMC-AS (0.5 gm, 1 time) and citric acid hydrate (0.1 gm, 20%) in 90% ethanol in water (15 ml, 30V) were heated at 65 to 70° C. to get clear solution. The content was stirred for 30 minutes at 25° C. to 30° C. To this, 1.0 g charcoal was added and stirred for 30 minutes at 80° C. The content was filtered through hyflosupercell, and the hyflosupercel pad is washed with 50 mL ethanol. The filtrate was concentrated under vacuum below 45° C. till 100 mL ethanol remains. 50 mL ethanol was added and stirred at 70° C. to get clear solution, followed by spray drying in JISL Mini spray drier LSD-48 under the below conditions. The product was collected from cyclone and was further dried at 40° C.±5° C. under vacuum for 4 hours to obtain the title compound in substantially pure amorphous form.

| Sr. No. | Parameters | Conditions |
| --- | --- | --- |
| a) | Feed pump | 30 rpm |
| b) | Inlet temperature | 60° C. |
| c) | Outlet temperature | 40° C. |
| d) | Aspirator rate | 1300 rpm |
| e) | Vacuum for conveying the dry product | 80 mm of Hg |
| h) | Hot air supply | 2 Kg/cm$^2$ |

The spray-dried dasatinib was amorphous in nature. The obtained product contains residual solvent well within ICH limit.

Example-26

Preparation of Amorphous Dasatinib

Dasatinib (60 gm, 0.123 mol) and HPMC-AS (60 gm, 1 time) were placed in 250 ml in grinding bowl of ball mill with 188 no's of stainless steel balls. The grinding bowl was fitted into Ball Mill. The Ball milling was started with set time of 60 min at 100 rpm and interval time of 10 min. The milling was continued for 7 hours. The product was unloaded to get 110.1 gm dasatinib amorphous form with 91.8% yield. The obtained product contains residual solvent well below ICH limit having 99.90% purity by HPLC. (FIG. 12: XRD).

While the present invention has been described in terms of its specific embodiments, certain modifications and equivalents will be apparent to those skilled in the art and are intended to be included within the scope of the present invention.

We claim:

1. A process for the preparation of the amorphous form of dasatinib of Formula (I),

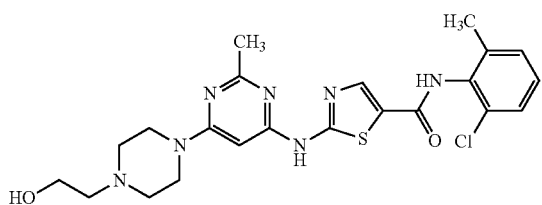 (I)

wherein the amorphous form is prepared by grinding a solid-solid mixture of dasatinib and a polymer.

2. The process according to claim 1, wherein the amorphous dasatinib is free from residual solvents.

3. The process according to claim 1, wherein the polymer is a non-ionic polymer or an ionic polymer.

4. The process according to claim 1, wherein the amorphous form is prepared by grinding dasatinib of Formula (I) in the absence of a solvent.

5. The process according to claim 1, further comprising forming a pharmaceutical composition comprising the amorphous form of dasatinib of Formula (I) with one or more pharmaceutically acceptable carriers, excipients or diluents.

6. The process according to claim 1, further comprising forming A pharmaceutical composition comprising a therapeutically effective amount of the amorphous form of dasatinib of Formula (I), the polymer and one or more pharmaceutically acceptable carriers, excipients or diluents.

7. The process according to claim 1, wherein grinding the solid-solid mixture is under controlled humidity.

8. The process according to claim 1, wherein the amorphous dasatinib is free from residual solvents, and the amorphous form of dasatinib is stable as measured by absence of a conversion of the amorphous form of dasatinib to a crystalline form of dasatinib after the amorphous form of dasatinib is exposed to a relative humidity of 75% at 40° C. or 60% at 25° C. for a period of at least three months.

9. The process according to claim 1, wherein the amorphous form of dasatinib is stable as measured by absence of a conversion of the amorphous form of dasatinib to a crystalline form of dasatinib after the amorphous form of dasatinib is exposed to a relative humidity of 75% at 40° C. or 60% at 25° C. for a period of at least three months.

10. The process according to claim 7, wherein the controlled humidity is a relative humidity in the range of 50±10%.

11. The process according to claim 1, wherein the step of grinding a solid-solid mixture of dasatinib and a polymer comprises grinding a solid-solid mixture of crystalline dasatinib and HPMC-AS.

12. The process according to claim 1, wherein the step of grinding dasatinib comprises grinding crystalline dasatinib.

13. The process according to claim 1, wherein the polymer comprises one or more of HPMC-AS, HPMC, methacrylic acid copolymers, and PVP.

14. The process according to claim 1, wherein the ratio of dasatinib to polymer is about 1:1 to about 1:10.

* * * * *